(12) United States Patent
Greiser et al.

(10) Patent No.: US 9,689,951 B2
(45) Date of Patent: Jun. 27, 2017

(54) PHASE-CONTRAST MR IMAGING WITH SPEED ENCODING

(71) Applicant: Siemens Aktiengesellschaft, Munich (DE)

(72) Inventors: Andreas Greiser, Erlangen (DE); Jana Hutter, Effeltrich (DE); Peter Schmitt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 488 days.

(21) Appl. No.: 14/472,599

(22) Filed: Aug. 29, 2014

(65) Prior Publication Data

US 2015/0061671 A1  Mar. 5, 2015

(30) Foreign Application Priority Data

Aug. 30, 2013  (DE) .......................... 10 2013 217336

(51) Int. Cl.
| | |
|---|---|
| *G01V 3/00* | (2006.01) |
| *G01R 33/563* | (2006.01) |
| *A61B 5/055* | (2006.01) |
| *G01R 33/561* | (2006.01) |
| *A61B 5/026* | (2006.01) |

(52) U.S. Cl.
CPC ...... *G01R 33/56316* (2013.01); *A61B 5/0263* (2013.01); *A61B 5/055* (2013.01); *G01R 33/5611* (2013.01)

(58) Field of Classification Search
CPC .............. G01R 33/543; G01R 33/5659; G01R 33/3415; G01R 33/36; A61B 5/055
USPC ................................................. 324/309, 318
See application file for complete search history.

(56) References Cited

U.S. PATENT DOCUMENTS

| | | | |
|---|---|---|---|
| 8,150,491 B2* | 4/2012 | Jung ................... | G01R 33/5611 345/418 |
| 2013/0049752 A1* | 2/2013 | Hutter ................ | G01R 33/5611 324/309 |

OTHER PUBLICATIONS

Otazo ; "Low-Rank and Sparse Matrix Decomposition for Accelerated Dynamic MRI"; Tagungsbeitrag 35th Annual International IEEE EMBS Conference; 2013;.
Tremoulheac et al.; "Dynamic MR image reconstruction-separation from under-sampled (k-t)-space via low-rank plus sparse prior"; Journal of Latex Class Files; vol. 11; No. 4; pp. 1-13; (2012).
Lingala et al., "Accelerated Dynamic MRI Exploiting Sparsity and Low-Rank Structure: k-t SLR"; IEEE Transactions on Medical Imaging; vol. 30; No. 5; pp. 1042-1054;(2011).

(Continued)

*Primary Examiner* — Walter L Lindsay, Jr.
*Assistant Examiner* — Frederick Wenderoth
(74) *Attorney, Agent, or Firm* — Schiff Hardin LLP

(57) ABSTRACT

MR signals are acquired with a method for phase contrast magnetic resonance (MR) imaging with speed encoding, in order to acquire raw data for multiple MR images. The multiple MR images are reconstructed. For this purpose, matrix elements are determined for numerous matrices, wherein the sum of the numerous matrices results in a pixel matrix. The pixel matrix has matrix elements that represent the pixel values for a reference MR image with flow compensation. The pixel matrix has further matrix elements that represent the pixel values for the at least one MR image with speed encoding. The matrix elements of the numerous matrices are determined such that a first matrix of the numerous matrices fulfills a first condition.

16 Claims, 7 Drawing Sheets

(56) References Cited

OTHER PUBLICATIONS

Zhan et al., "Separating Sparse and Low-Dimensional Signal Sequences from Time-Varying Undersampled Projections of their Sums"; Tagungsbeitrag IEEE International Conference an Acoustics, Speech and Signal Processing (ICASSP), (2013).

* cited by examiner

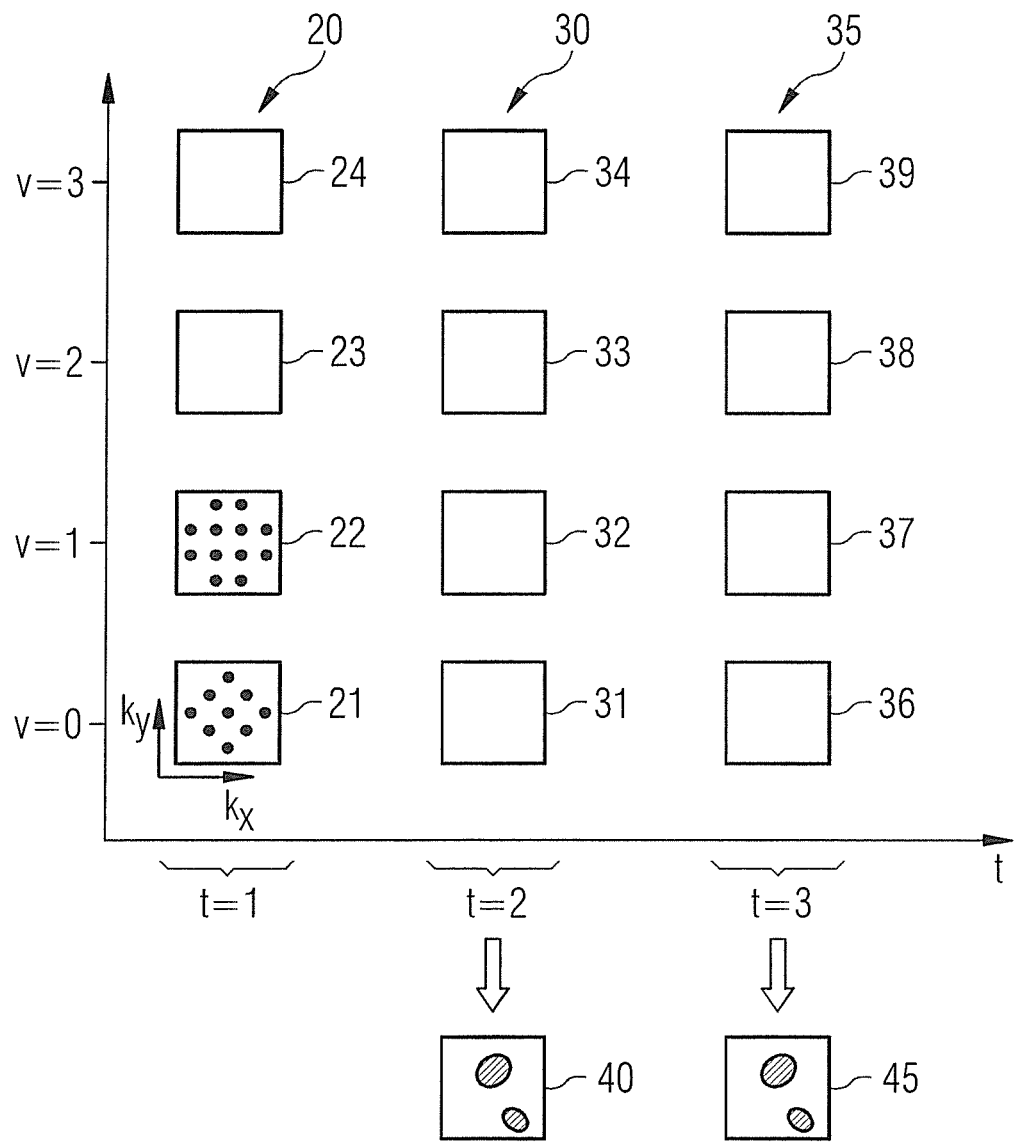

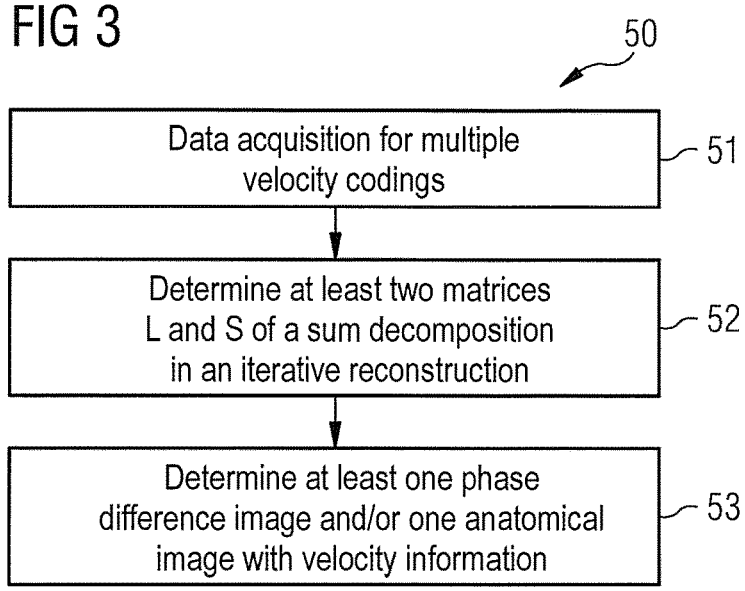
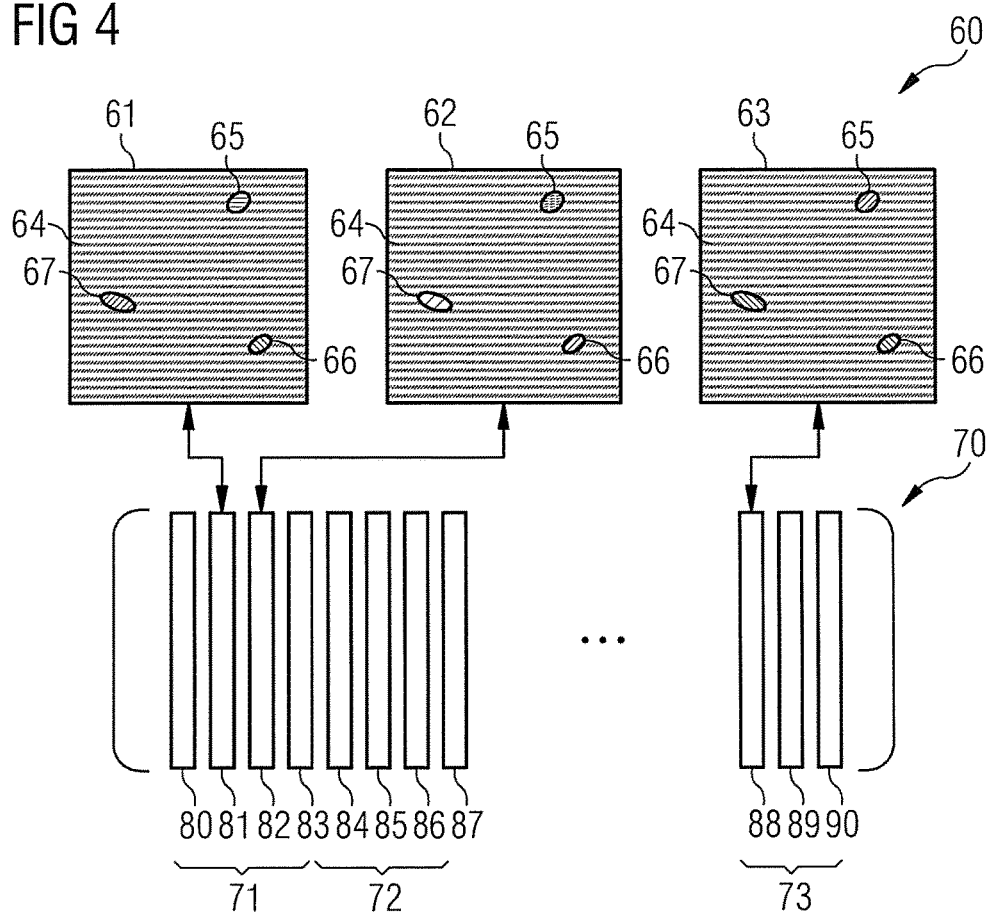

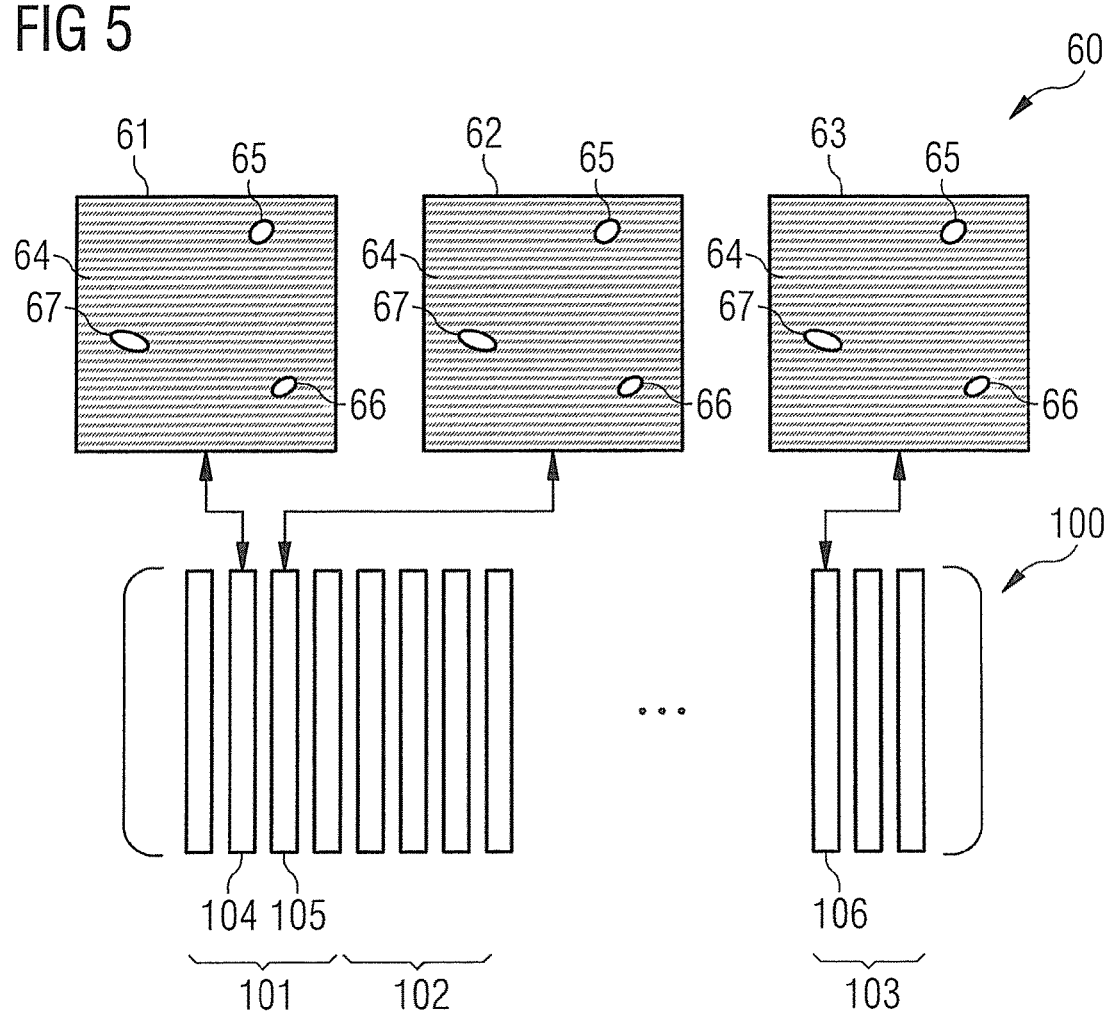

PHASE-CONTRAST MR IMAGING WITH SPEED ENCODING

BACKGROUND OF THE INVENTION

Field of the Invention

The invention relates to a method for creating magnetic resonance (MR) images of an object under examination and a magnetic resonance apparatus for implementing such a method. The invention relates, in particular, to methods and MR apparatuses that enable imaging of flow rates.

Description of the Prior Art

The spatially and temporally resolved imaging of flow rates has numerous applications, such as examining the aorta, the carotids, and/or the heart, for example. A multi-dimensional phase contrast MR imaging can be used for measuring flow rates. For a time-resolved determination of the speed, numerous raw data sets must be recorded (acquired) in each examination. In addition to an acquisition with flow compensation, at least one further acquisition occurs, in which a speed encoding gradient or numerous speed encoding gradients are switched on and off, such that, for example, speeds along a specific spatial direction are acquired. The large amount of data that must be acquired (two to three spatial directions, speed encoding in one or more spatial directions, and optionally a temporal resolution) leads to long data acquisition times.

In order to reduce the data acquisition time, methods with sub-scanning have been developed into valuable and promising procedures. Methods of this type can also be implemented as parallel imaging methods, in which data are acquired with multiple antennas. The use of conventional SENSE ("Sensitivity Encoding") or GRAPPA ("Generalized Autocalibrating Partially Parallel Acquisition") methods can result in the speed factors being not particularly large and/or the contrast/noise ratio being strongly degraded in an imaging with speed encoding.

DE 10 2011 081 411.6 describes techniques for an MR imaging, in which the MR images are created with iterative reconstruction methods. Various scanning patterns are combined with one another thereby, in order to improve the quality of the reconstructed MR images, even with stronger sub-scanning.

With technologies for iterative reconstruction, matrix elements of a pixel matrix are determined. The pixel matrix can contain pixel values for numerous MR images thereby, which correspond to various speed encodings and/or various times. Many of the conventional technologies for iterative reconstruction do not exploit the fact that stationary tissues and regions having flowing nuclear spins result in specific characteristics of a pixel matrix of this type. Because the various signal contributions from stationary tissues and regions having flowing nuclear spins cannot be systematically taken into account with conventional technologies for iterative reconstruction, reduces the quality of the spatially resolved speed data that can be determined from the reconstructed MR images is reduced when stronger sub-scanning is implemented. Conversely, the time required for the data acquisition is frequently relatively long if flow data are to be determined with an adequate quality.

BRIEF SUMMARY OF THE INVENTION

An object of the present invention is to provide methods and devices for phase contrast MR imaging with speed encoding that enable a reconstruction of MR images having an adequate quality, even in the case of strong sub-scanning.

According to one aspect of the invention, in a method and a magnetic resonance apparatus for phase contrast magnetic resonance (MR) imaging with speed encoding, MR images are reconstructed in an iterative reconstruction procedure. With the reconstruction of MR images, which are acquired with different speed encodings and, optionally, at different times, the matrix elements of numerous matrices are determined, which represent a breakdown of the sums for a pixel matrix. The reconstruction can occur such that matrix elements of a first matrix and matrix elements of a second matrix are determined, the sum of which is the pixel matrix. The pixel matrix contains matrix elements that are the pixel values of an MR image with flow compensation, and further matrix elements that are the pixel values of at least one MR image with speed encoding. For a time-resolved phase contrast MR imaging, the pixel matrix contains the matrix elements of the MR image with flow compensation and the at least one MR image with speed encoding, for different times in each case.

The first matrix can be subject to a first constraint, which is taken into account in the determination of the first matrix and the second matrix. The first constraint can depend on an order of the first matrix, such that signal contributions that vary as a function of time and/or as a function of the speed encoding are suppressed in the first matrix.

The second matrix can be subject to a second constraint, which is taken into account in the determination of the first matrix and the second matrix. The second constraint can be dependent on whether the second matrix is sparsely populated, or can be transformed into a sparsely populated matrix. This ensures that the second matrix represents signal contributions from regions of an object under examination having flowing nuclear spins. This ensures that the second matrix contains signal portions that vary as a function of time and as a function of the speed encoding. The second matrix is determined such that signal contributions from regions that do not vary as a function of time and as a function of the speed encoding are suppressed.

Signal contributions that "vary as a function of the speed encoding," as used herein are dependent on whether the data acquisition occurs with flow compensation or with speed encoding (thus, whether or not any speed encoding occurs), and that are further dependent on which speed encoding is used.

With methods and devices according to exemplary embodiments, a breakdown (deconstruction or decomposition) of the sums for the pixel matrix into a first matrix of a low order and a second matrix that is sparsely populated, or can be transformed to a sparsely populated matrix, can first occur for the reconstruction of the MR images. The pixel matrix can subsequently be calculated as the sum of the first matrix and the second matrix.

A method for phase contrast MR imaging with speed encoding according to one embodiment includes detecting MR signals in at least one time period, in order to acquire the raw data in each of the time periods of the at least one time period for multiple MR images. The multiple MR images include, in each case, a reference MR image with flow compensation and at least one MR image with speed encoding, for each time period. The method includes a reconstruction of multiple MR images for the numerous time periods. The reconstruction includes a determination of matrix elements of numerous matrices, wherein the sum of the numerous matrices results in a pixel matrix, which contains pixel values for the reference MR image and pixel values for the at least one MR image with speed encoding as matrix elements in each case for each of the time periods of the at least one time period. The matrix elements of the numerous matrices are determined such that a first matrix of the numerous matrices fulfills a first condition.

With the method, the reconstruction includes the determination of the matrix elements of numerous matrices, which represents a breakdown of the sums for the pixel matrix. This already enables the systematic taking into account of the different contributions from nuclear spins in stationary tissues and regions having flowing nuclear spins, during the reconstruction procedure. Signal contributions from stationary tissues vary only slightly, or not at all, in the MR images, as a function of time and for different flow compensations or speed encodings, such that these portions can already be determined in the reconstruction by means of the first condition. Signal contributions from regions having moving nuclear spins vary to a greater degree in different time periods and depending on the speed encoding, but concern only a smaller number of pixels in each MR image.

The acquisition of raw data can occur for numerous different time periods, in order to execute a time-resolved phase contrast MR imaging. Accordingly, the reconstruction can occur such that, in each case, the reference MR image and the at least one image with speed encoding can be determined in a time-resolved manner. The pixel matrix contains matrix elements that are, in each case, the pixel values for the reference MR image, and the at least one MR image with speed encoding, for each of a number of time periods.

The first condition can be selected such that the first matrix represents stationary tissue. The first condition can be selected such that signal portions that can vary as a function of time and/or as a function of the speed encoding are suppressed in the first matrix.

The first condition can be dependent on an order of the first matrix. As a result, it is possible to take into account that the pixel values in the MR images, which correspond to different time periods, vary only slightly, or not at all, if the pixels in question represent stationary tissues.

The first condition ensures that the order of the first matrix is as low as possible. The first condition can ensure, for example, that the order for the first matrix is lower than a threshold value.

With the method, a breakdown of the pixel matrix into exactly two matrices, the first matrix and a second matrix, can be determined. The number of the numerous matrices can be two. The first matrix and the second matrix can be defined such that a sum of the first matrix and the second matrix is the pixel matrix.

The matrix elements of the numerous matrices can be determined such that the second matrix fulfills a second condition, which differs from the first condition.

The second condition can be selected such that the second matrix represents data regarding regions of an object under examination having flowing nuclear spins.

The second condition can be a constraint, which ensures that the second matrix can be transformed into a matrix having a population density that is smaller than a further threshold value.

The first matrix and the second matrix can have the same number of columns and the same number of rows as the pixel matrix.

The first matrix, the second matrix, and the pixel matrix can each have $(N_v+N_c)*N_t$ columns and N rows, wherein $N_v$ is the number of different speed encodings for each time period, $N_c$ is the number of different flow compensated recordings for each time period, $N_t$ is the number of different time periods, and N is the number of pixels in each MR image. Accordingly, $N_v$ represents the number of different speed encodings. The number $N_c$ represents the number of different recordings with flow compensation, which are carried out for each time period. As an example, $N_c$ can be 1, plus at least one recording with flow compensation. The N pixel values of an MR image can, in each case, be contained in one column. Different columns correspond to different times and/or different speed encodings.

Other matrix forms may be used. The first matrix, the second matrix, and the pixel matrix can each, for example, contain $(N_v+N_c)*N_t$ rows and N columns. The N pixel values of an MR image can, in each case, be contained in a row of the pixel matrix. Different rows correspond to different times and/or different speed encodings.

The matrix elements of the first matrix and the matrix elements of the second matrix can be determined through minimization of a target function.

The target function can have at least one first regularization term dependent on the matrix elements of the first matrix, and at least one second regularization term dependent on the matrix elements of the second matrix.

The target function can have a further term, which is dependent on the first matrix, the second matrix and the raw data. The further term can be dependent on a reconstruction matrix, which is dependent on sub-scanning patterns that are used for the different time periods and for the different speed encodings. The reconstruction matrix can be dependent on sensitivity charts of receiver coils.

The further term can be a so-called data fidelity term, which is dependent on an $L_2$ norm for a deviation between the raw data expected for the first matrix and the second matrix, and the actual recorded raw data for the different time periods and the different speed encodings. With the data fidelity term is it is possible to ensure that the pixel values contained in the pixel matrix for the different times and speed encodings reproduce the actual recorded raw data well.

The at least one first regularization term can be independent of the matrix elements in the second matrix.

The at least one second regularization term can be independent of the matrix elements in the first matrix.

The first regularization term can be dependent on a norm for the first matrix, which is different than an $L_2$ norm.

The second regularization term can be dependent on a norm for the second matrix, which is different than an $L_2$ norm.

The first regularization term can be dependent on a nuclear norm for the first matrix.

The second regularization term can comprise a TV ("total variation") regularization term and/or an L1 regularization term dependent on the matrix elements of the second matrix.

As a result of minimizing the target function with the corresponding regularization terms, conditions for the first matrix and/or the second matrix can be imposed, which ensure that the first matrix primarily represents signal portions that are not, or are only slightly, dependent on time and the speed encodings. Furthermore, it can be ensured that the second matrix primarily represents signal contributions from regions of an object under examination, which can vary as a function of time and the speed encoding.

The matrix elements of the first matrix and the matrix elements of the second matrix can be determined in an iterative procedure. Both actualized values for the matrix elements of the first matrix as well as actualized values for the matrix elements of the second matrix can be determined thereby in each iteration. In other embodiment examples, actualized values for the matrix elements of the first matrix and/or actualized values for the matrix elements of the second matrix can be determined, not in each iteration, but rather, for example, only in each $k^{th}$ iteration, wherein k>1.

After the determination of the matrix elements for the first matrix and the matrix elements for the second matrix, the pixel matrix can be determined as the sum of the first matrix and the second matrix.

A flow pattern for flowing nuclear spins can be determined, dependent on the pixel matrix. For this, a phase difference image can be determined for at least one time period from a reconstructed MR image with speed encoding and the corresponding reference MR image with flow compensation.

In the detecting of MR signals for acquiring the raw data, a raw data space can be sub-scanned. For at least one of the time periods, both the data acquisition with flow compensation, as well as the data acquisition with speed encoding can occur with a sub-scanning. For each time period, both the data acquisition with flow compensation as well as the data acquisition with speed encoding can occur with a sub-scanning. Different scanning patterns for the sub-scanning in the raw data space can be used in a time period for the data acquisition with flow compensation and the data acquisition with different speed encodings. Alternatively, or in addition thereto, different scanning patterns can be used for the sub-scanning in the raw data space for different time periods. As an example, scanning patterns can be permuted as a function of the speed encoding and/or time.

The detection of MR signals can be carried out as a parallel data acquisition with numerous receivers, e.g. numerous receiver coils.

Another aspect of the invention is a magnetic resonance apparatus for phase contrast magnetic resonance (MR) imaging with speed encoding. The magnetic resonance apparatus has a data acquisition unit (scanner), which is equipped for detecting MR signals with at least one antenna in at least one time period, in order to acquire, in each of the time periods of the at least one time period, raw data for a multiple MR images. The multiple MR images for each time period can include, in each case, a reference MR image, which is recorded with a flow compensated recording sequence, and at least one MR image with speed encoding. The magnetic resonance apparatus has an image processor for reconstructing the numerous MR images from the acquired raw data for each of the time periods of the at least one time period. The image processor is equipped for determining matrix elements of numerous matrices, such that the sum of the numerous matrices results in a pixel matrix, the matrix elements of which represent the reference MR image, and the pixel elements of the at least one MR image with speed encoding, in each case for the numerous time periods, and that fulfills a first condition for a first matrix of the numerous matrices.

Further features of the MR apparatus according to embodiment examples correspond to the method features described above.

The MR apparatus can be configured for time-resolved phase contrast MR imaging. For this purpose, the scanner can be configured to detect MR signals in numerous time periods with a least one antenna. The image processor can be configured to determine the matrix elements of the numerous matrices such that the sum results in a pixel matrix that contains pixel values of a reference MR image with flow compensation and at least one MR image with speed encoding, in each case for numerous time periods, as the matrix elements.

The MR apparatus can have multiple antennas (reception channels) for a parallel data acquisition.

With the MR apparatus according to the embodiment examples, the image processor can be configured to execute a data processing for determining the numerous matrices in accordance with the method according to the embodiment examples.

With the MR apparatus according to the embodiment examples, the antenna can be configured to execute a data acquisition in accordance with the further features of the method according to the described embodiments.

With devices and methods according to the embodiments described above, the characteristics of different matrices can take into account a sum breakdown of a pixel matrix in the computer reconstruction of the MR images. As a result, it is systematically taken into account that the small influence of temporal dependency and/or different speed encodings in stationary tissues results in the corresponding signal portions forming a matrix having a low order. The signal contributions from regions having flowing nuclear spins vary more strongly as a function of time and/or as a function of the speed encoding, but concern only a smaller number of pixels.

The systematic taking into account of the characteristics of the addends of the pixel matrix enables a reliable reconstruction, even with stronger sub-scanning. Time-resolved flow images of sufficient quality can be determined even with stronger sub-scanning.

BRIEF DESCRIPTION OF THE DRAWINGS

FIG. 2 schematically shows raw data sets, which are acquired with embodiments of the method according to the invention.

FIG. 3 is a flowchart of an embodiment of the method according to the invention.

FIG. 4 illustrates a pixel matrix for which, in an embodiment of the method according to the invention, a breakdown is determined, wherein a column of the pixel matrix, in each case, contains all of the pixel values for an MR image.

FIG. 5 illustrates a first matrix, which is determined, in an iterative reconstruction in an embodiment of the method according to the invention.

DETAILED DESCRIPTION OF THE INVENTION

Figure 1:
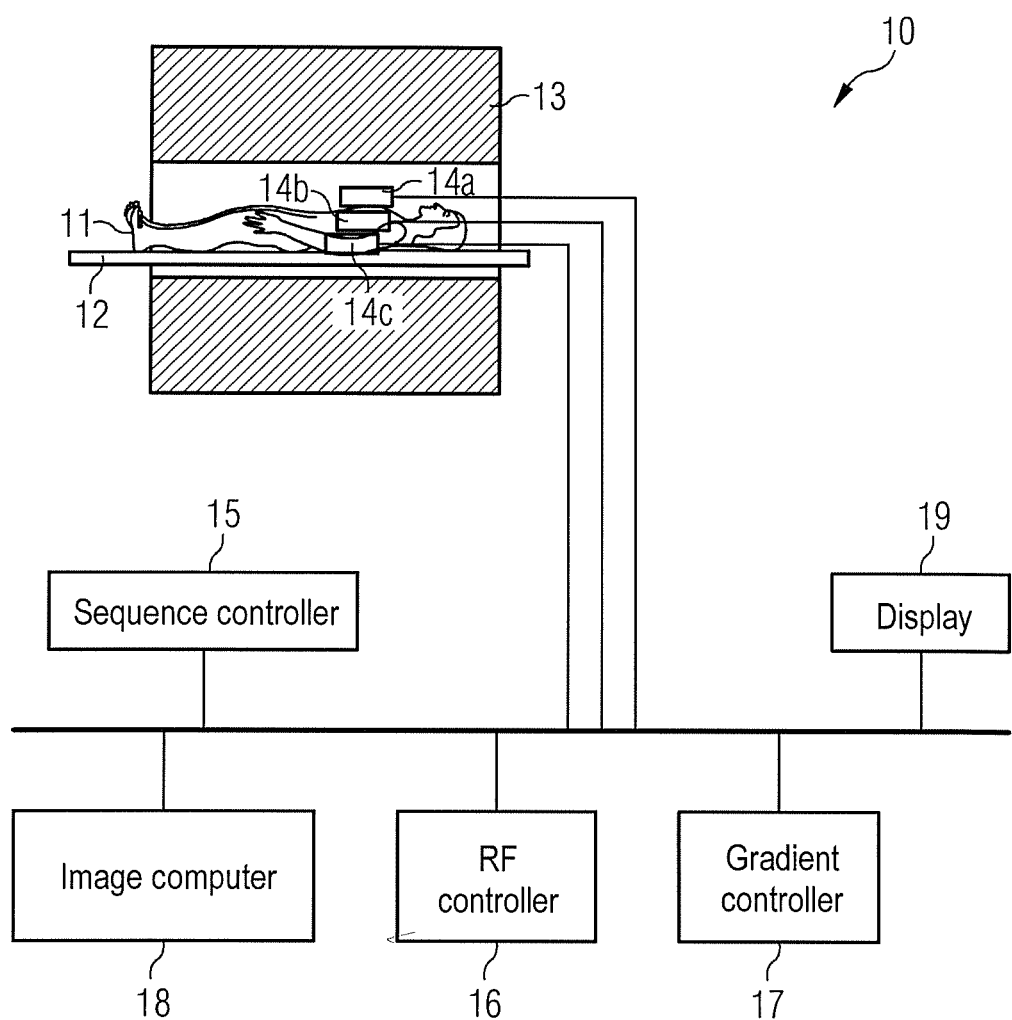
FIG. 1 schematically shows an MR apparatus having an image processor, which is configured for executing embodiments of the method according to the invention.

FIG. 1 shows an MR apparatus 10, with which MR images of an object under examination 11, disposed on a bed 12, can be recorded. The magnetization generated by a magnet 13 is spatially encoded and deflected by switching on and off magnetic field gradients and RF pulses, wherein the MR signals are detected with an antenna or with numerous antennas 14a-14c. The antennas 14a-14c can be designed as an MR signal coil, or can be numerous MR signal coils, which are disposed surrounding the object under examination 11.

A sequence controller 15 controls the switching on and off of the magnetic field gradients, the RF pulses, and the signal readout, in dependence on the selected imaging sequence, and establishes the sequence of the gradient switching on and off, the irradiation of the RF pulses, and the readout of signals. The sequence controller 15 controls an RF control unit 16, which in turn is responsible for controlling the irradiated radio-frequency pulses. A gradient control unit 17 is responsible for the switching on and off of the magnetic field gradients, which, for example, can be predefined by the sequence control unit 15.

An image processor 18 computes MR images from the MR signals detected with the at least one receiver 14a-14c. The MR images can be reconstructed with iterative reconstruction methods, as shall be explained in greater detail below. The MR images generated by the image processor 18 can be displayed on a display screen 19. An operator can control the MR apparatus 10 by means of an input unit. The functions of the sequence control unit 15, the RF control unit 16, the gradient control unit 17 and/or the image processor 18 can also be executed by the same unit, e.g. a computer, which is configured for executing the aforementioned control and evaluation steps.

According to embodiment examples of the invention, the MR apparatus 10 is configured for executing a time-resolved phase contrast MR imaging with speed encoding. In order to obtain data regarding a blood flow or a flowing substance in the object under examination 11, speed encoding gradients are switched on and off. For numerous successive time periods, at least one data acquisition with flow compensation is executed in each case. Furthermore, for each of the numerous time periods, at least one acquisition is executed in each case, for spins flowing in a speed encoding direction. The speed encoding gradient can be switched on and off, such that a speed encoding is obtained, for example, along a predefined speed encoding direction. The corresponding technologies and sequences are known to those skilled in the art, and need not be explained in detail herein. Likewise, the manner by which MR signals can be detected using the sequence of magnetic field gradients and irradiation of RF pulses is known to those skilled in the art, so such techniques need not be explained in detail herein.

The data acquisition can be coordinated to a physiological cycle. As an example, an EKG triggering or pulse triggering can be used in order to execute the data acquisition in coordination with a cardiac cycle.

As is described in detail with reference to FIG. 2-FIG. 8, the image processor 18 is configured according to embodiment examples, for computing an iterative reconstruction of matrix elements of numerous matrices, the sum of which results in a pixel matrix. The pixel matrix has matrix elements that can correspond to the pixel values of MR images for different speed encodings and, optionally, for different times as well. The image processor 18 can be configured for computing a first matrix and a second matrix, the sum of which results in the pixel matrix. In the determination of the first matrix and the second matrix, the image processor 18 can take into account different constraints, which are to be applied to the first matrix and the second matrix.

The image processor 18 determines the first matrix and the second matrix by solving an optimization problem with which, for example, a first regularization term ensures that an order and/or, for example, a nuclear norm of the first matrix is low. Alternatively or in addition, a second regularization term can ensure that the second matrix is sparsely populated, or can be transformed to a sparsely populated matrix.

In this manner, the image processor 18 can systematically exploit the fact, in the reconstruction of the MR images that stationary tissues result in pixel values that do not vary as a function of time and as a function of the speed encoding, or vary only slightly. A first matrix, which primarily represents the signal portions of stationary tissues, has a low order.

The image processor can, alternatively or additionally, exploit the fact that regions having flowing nuclear spins deliver different signal portions for the different time periods and/or different speed encodings, which thus vary as a function of time and the speed encoding. Regions having flowing nuclear spins are usually present, however, only in a limited portion of the pixels. A second matrix, which primarily represents signal portions that vary as a function of time and the speed encoding, can be transformed into a sparsely populated matrix by means of a suitable transformation.

In order to simplify the terminology, those signal contributions that are referred to as "varying as a function of the speed encoding" shall be referred to as those signal contributions that vary depending on whether the acquisition occurs with flow compensation, and furthermore are dependent on which speed encoding is used. The corresponding signal contributions thus depend on whether any recording with speed encoding is present, and, if so, which speed encoding is present.

Accordingly, those signal portions that are referred to as signal portions that "do not vary as a function of the speed encoding" are those signal portions that are not dependent on whether the acquisition occurs with flow compensation or with speed encoding, and that furthermore are not dependent on which speed encoding is used.

FIG. 2 schematically shows data sets acquired and processed with the method according to embodiment examples. Data sets for a flow compensated recording sequence and for at least one speed encoding are recorded for each of numerous successive time periods. The time periods are indicated with the index t. The different speed encodings are indicated with the index v. The index v=0 corresponds to a data acquisition with a flow compensated recording sequence. In the following, as an example, the case having only one flow compensated recording for each time period shall be explained. Numerous recordings with flow compensation can also be carried out in each time period, wherein then, corresponding to $N_c$, the possible index values for v indicate the flow compensated recordings. For this, $N_c$ is the number of flow compensated recordings for each time period.

In a time period t=1, numerous raw data sets 20 are recorded. One raw data set 21 is recorded with a flow compensated (i.e. flow sensitive) recording sequence. Additionally, at least one further raw data set 22 is recorded such that spins moving along one direction are detected. For this, a speed encoding along a first spatial direction can be set that is the speed encoding direction for this data acquisition.

As is schematically depicted in FIG. 2, more than one raw data set having a flow sensitive data acquisition can be recorded in each time period. For example, the further data set 23 can be recorded with a flow sensitive data acquisition, such that a speed encoding along a second spatial direction can be set. The further raw data set 24 can be recorded with a flow sensitive data acquisition, such that a speed encoding along a third spatial direction can be set. The first, second and third spatial directions can be orthogonal in relation to one another.

Accordingly, numerous raw data sets 30, 35 can be recorded, in each case, in later time periods t=2 and t=3. In each case, a flow compensated, i.e. flow sensitive, data acquisition is used, in order to record a raw data set 31 and a raw data set 36. Flow sensitive data acquisitions are used to record raw data sets 32-34 and 37-39.

For each time period and/or both for the recording with flow compensation as well as for each recording with speed encoding, the data acquisition can occur, in each case, as parallel data acquisitions with numerous receivers. Accordingly, points in the raw data space can be scanned in parallel, in each case with numerous receivers, in order to execute a parallel data acquisition.

With each data acquisition, a raw data space can be sub-scanned, such that it is incompletely filled with raw data. This is schematically depicted for the raw data sets 21, 22. Scanning patterns that are used for the sub-scanning in the raw data space, i.e. in k-space, can differ as a function of the speed encoding (i.e. for each different v) and/or as a function of the time period (i.e. for each different t). As an example, numerous scanning patterns can be permuted as a function of the speed encoding and/or time in the corresponding data acquisition.

Although in FIG. 2 a two-dimensional raw data space is schematically depicted, the described methods and MR apparatuses can also be used for a data acquisition in three spatial directions. The corresponding data can be recorded in parallel with numerous receivers.

The reconstruction of MR images for the different time periods t=1, 2, . . . , $N_t$ and the different flow compensated recordings, and recordings with speed encodings, v=0, 1, . . . , $N_v$, can occur by iterative reconstruction.

In the reconstruction of the MR images, pixel values $x_i^{t,v}$ are determined, wherein i indicates an index that defines the position of the pixel in an MR image. An index for the time period, in which the data of the corresponding MR image were acquired, is indicated by t. An index that shows whether the pixel corresponds to a flow compensated recording (v=0) or a recording with a speed encoding (v=1, . . . ) is indicated by v.

The corresponding pixel values for the numerous MR images for numerous time periods, in each case, can be depicted in a matrix having the form $$M = \begin{pmatrix} x_1^{1,0} & x_1^{1,1} & \cdots & x_1^{1,Nv} & x_1^{Nt,0} & x_1^{Nt,1} & \cdots & x_1^{Nt,Nv} \\ \vdots & \vdots & \ddots & \vdots & \cdots & \vdots & \vdots & \ddots & \cdots \\ x_N^{1,0} & x_N^{1,1} & \cdots & x_N^{1,Nv} & x_N^{Nt,0} & x_N^{Nt,1} & \cdots & x_N^{Nt,Nv} \end{pmatrix} \quad (1)$$

This matrix is referred to here as a pixel matrix. The matrix elements $x_i^{t,v}$ i.e. the pixel values of the different MR images, are complex numbers thereby. The number N, the maximum value of the index for the position of a pixel in an MR image, is selected such that N pixels are present for each MR image. All pixel values in an MR image can thus, in the matrix depiction of equation (1), be contained in exactly one row of the pixel matrix M. For each time period, a total of raw data for $N_v+1$ MR images are recorded, wherein $N_v+1 \geq 2$. For each time period, at least one recording with flow compensation and at least one recording with speed encoding occurs.

Numerous matrices are determined with methods and devices according to embodiment examples, the sum of which results in the pixel matrix. In particular, a first matrix L and a second matrix S can be determined, which fulfill $$M=L+S \quad (2)$$

The matrices L and S represent a sum breakdown of the pixel matrix M. The first matrix L and the second matrix S have the same number of columns as the pixel matrix M. The first matrix L and the second matrix S have the same number of rows as the pixel matrix M. As an example, the pixel matrix M, the first matrix L, and the second matrix S can be determined such that the number of columns in each case is $(N_v+1)*N_t$, wherein $N_t$ is the number of time periods for which, in each case, a data acquisition occurs. The quantity $N_v+1$ is the number of raw data sets for each time period for a recording with a flow compensated recording sequence and at least one recording with speed encoding. The acquisition of a raw data set can occur in parallel with numerous receivers.

Matrix elements of the matrices L and S can be determined with the methods and apparatuses according to the described embodiments, such that signal portions that can vary as a function of time and as a function of the speed encoding are suppressed in the first matrix L.

Matrix elements of the matrices L and S can be determined with the methods and apparatuses according to embodiment examples, such that signal portions that do not vary as a function of time and as a function of the speed encoding are suppressed in the second matrix S.

The first matrix L and the second matrix S can be determined such that the first matrix L fulfills a first condition and/or the second matrix S fulfills a second condition, while the sum L+S reproduces the recorded data well. The first matrix L can be subject to the first condition, which it is a matrix of a low order. As an example, the first matrix L can be determined under the condition that the first matrix L has an order that is less than $\alpha*(N_v+1)*N_t$, wherein a is a multiplier that is less than 1. The first matrix L can be determined under the condition that a nuclear norm of the first matrix L is less than a threshold value. In this manner, it is possible to obtain that the first matrix L primarily represents signal portions that can vary as a function of time and as a function of the speed encoding.

The second matrix S can be subject to the second condition, that it can be transformed into a sparsely populated matrix. The corresponding transformation, which transforms the second matrix S into a sparsely populated matrix, can be, for example, a difference between the MR image data for successive time periods, a wavelet transformation, a Fourier transformation, a filtering, or another transformation, which suppresses portions that do not vary as a function of time or as a function of the speed encoding. In this manner it is possible to obtain that the second matrix S primarily represents data concerning the variable signal portions from regions of the object under examination having flowing nuclear spins. These signal portions vary as a function of time t, and dependent on whether a recording occurs with flow compensation or speed encoding, and which speed encoding is used.

The determination of the first matrix L and the second matrix S such that their sum results in the pixel matrix, the first matrix L has a low order, and the second matrix S can be transformed to a sparsely populated matrix, is also referred to as an L-plus-S breakdown. This is used with methods and apparatuses according to embodiment examples on an MR phase contrast imaging such that the addends of a sum breakdown are determined for a pixel matrix M that contains the pixel values of MR images as matrix elements corresponding to the recording sequences with different speed encodings and, optionally, different times as well.

The first condition, to which the first matrix L is subjected, and the second condition, to which the second matrix S is subjected, can be imposed as constraints in an optimization procedure. Accordingly, an optimization with co-conditions can occur, such that the sum of the first matrix L and the second matrix S reproduce the recorded raw data well, while the constraints ensure that the order of the matrix L is low, and that the second matrix S can be transformed into a sparsely populated matrix.

The first condition can be obtained by means of a first regularization term. The first regularization term can be dependent on the order or the nuclear norm of the first matrix L. The second condition can be obtained by means of a second regularization term. The second regularization term can depend on a total variation (TV) norm and/or an $L_1$ norm from, for example, a wavelet transformation of matrix elements in the second matrix S.

The matrix elements of the first matrix L and the matrix elements of the second matrix S can be determined simultaneously. The first matrix L and the second matrix S can be determined simultaneously in an iterative reconstruction procedure, as shall be described in greater detail below.

Matrix elements for the pixel matrix M can be determined as a function of the first matrix L and the second matrix S in accordance with equation (2). The pixel matrix M contains the pixel values for the MR image with flow compensation and pixel values for at least one MR image with speed encoding as matrix elements for each of the numerous time periods.

Spatially resolved speed data can be obtained from these data. As an example, a phase contrast image can be computed in the conventional manner. This can be the computing of differences of a phase with a complex pixel value for and MR image with speed encoding, and a phase with a complex pixel value at the same pixel for the reference MR image with flow compensation. Alternatively, or additionally, an anatomic recording can be determined. This can be the computing of the quantity of a difference of a complex pixel value for an MR image with speed encoding and a complex pixel value at the same pixel for the reference MR image with flow compensation. The quantity for this difference can be computed for each speed encoding. The square of the quantity of the differences of the complex pixel values can be summed over the different speed encodings, and a square root of the sum can be computed in order to determine a pixel value for the anatomic image. In this manner, at least one phase contrast image 40, 45 and/or one anatomic image with speed data 40, 45, can be determined for each time period.

The reconstruction that can be carried out with methods and apparatuses according to embodiment examples shall be explained in greater detail with reference to FIG. 3-FIG. 7.

FIG. 3 is a flowchart for a method 50 according to an embodiment example. The method 50 can be automatically executed by the image processor 18.

The data acquisition occurs in each of numerous time periods in step 51. MR signals for a reference MR image are recorded thereby with a flow compensated recording sequence. MR signals for at least one MR image are recorded with a recording sequence with speed encoding. The corresponding raw data are recorded in a raw data space, which can be the k-space of a Fourier depiction. The data acquisition can occur for two or three spatial dimensions. The data acquisition can occur in each case with a sub-scanning.

At least one first matrix L and one second matrix S of a breakdown of a pixel matrix are determined in step 52. The first matrix L and the second matrix S are addends of a sum breakdown of the pixel matrix. The pixel matrix for which the sum breakdown is determined has column vectors or row vectors, which represent, in each case, the pixel values of an MR image for one of the time periods, and the flow compensated recording or one of the speed encodings. Accordingly, the first matrix L and the second matrix S can have column or row vectors, each of which represent different signal portions for one of the respective time periods and the flow compensated recording or one of the speed encodings.

The matrix elements of the first matrix L and the matrix elements of the second matrix S can be determined collectively in an iterative reconstruction. The iterative reconstruction can occur thereby such that the sum of the first matrix L and the second matrix S reproduces the raw data recorded in step 51 well, while the first matrix L satisfies a first condition, and the second matrix S satisfies a second condition. The first condition and the second condition can be constrained by means of corresponding regularization terms.

A further processing, as a function of the first matrix L and the second matrix S, can occur in step 53. Matrix elements of the pixel matrix M can be determined, in each case as the sum of a matrix element of the first matrix L and a matrix element of the second matrix S. The pixel values for the reference MR image with flow compensation and the at least one MR image with speed encoding can be read out of the pixel matrix M, in each case for each of the time periods.

A space- and time-resolved determination of a speed datum can contain the calculation of the difference of a phase of a pixel value for the corresponding pixel in an MR image with speed encoding and a phase of the corresponding pixel in a reference MR image with flow compensation, for numerous pixels, respectively. The space- and time-resolved determination of the speed datum can occur based on the at least one calculated phase difference image. An anatomic image with speed data can be calculated, in that, for the at least one speed encoding, in each case, the quantity, or the square of the quantity of the difference between a pixel value of the MR image with speed encoding and a pixel value of the reference MR image at the same pixel is calculated. If data are recorded with more than one speed encoding, the square of the quantity for the differences between pixel values can be added, and a square root of the sum can be calculated.

For each time period, the speed data can be determined in each case in a space-resolved manner. At least one speed datum can be determined in a time- and space-resolved manner for numerous time steps, respectively. The determination of the speed data can comprise a calculation of a speed vector and/or a calculation of at least one component of a speed vector and/or a calculation of an absolute quantity of a speed vector and/or a calculation of a derived value, in each case for numerous positions in the object under examination and for a plurality of time periods. The derived value can be the volumetric flow, the maximum flow or other stationary or time-resolved parameters.

FIG. 4 shows a number 60 of MR images 61-63. A first MR image 61 corresponds to a first time period and a first speed encoding. A second MR image 62 corresponds to the first time period and a second speed encoding. A third MR image 63 corresponds to another time period and the first speed encoding. Corresponding time-sequential MR images are reconstructed with methods and apparatuses according to embodiment examples, in each case for one recording with the flow compensated recording sequence, and optionally, for at least one further speed encoding, as well.

The MR images 61-63 each have one section that images stationary tissue 64. The MR images 61-63 have one section, or numerous sections, that represent the regions 65-67 of the object under examination with flowing nuclear spins. The regions 65-67 can comprise blood vessels, or are blood vessels, for example. The section that images the stationary tissue 64 varies only slightly, or not at all, as a function of time and the speed encoding. The regions 65-67 provide the signal that can vary as a function of time and as a function of the speed encoding, but concern only a small portion of the pixels of each MR image.

A pixel matrix 70 is depicted schematically. The pixel matrix 70 has numerous columns 80-90. One column 80 can represent the pixel values of an MR image for the first time period, and the flow compensated recording sequence. One column 81 can represent the pixel values of an MR image for the first time period and the first speed encoding. If the data acquisition occurs for numerous speed encodings, the pixel matrix 70 can have at least one further column 82, 83, which represents the pixel values of the MR image for the first time period. The additional column 82 can correspond to the pixel values of an MR image for the first time period and a second speed encoding. The additional column 83 can correspond to the pixel values of an MR image for the first time period and a third speed encoding.

One column 84 of the pixel matrix 70 can represent the pixel values of an MR image for the second time period and the flow compensated recording sequence. One column 85 can represent the pixel values of an MR image for the second time period and the first speed encoding. If the data recording occurs for more than one speed encoding, the pixel matrix 70 can have at least one further column 86, 87 that represents the pixel values of the MR image for the second time period. The additional column 86 can correspond to the pixel values of an MR image for the second speed encoding. The additional column 87 can correspond to the pixel values of an MR image for the third speed encoding.

The pixel matrix 70 can have further columns, in which the pixel values of the corresponding MR image are contained for each of the time periods for which a data acquisition occurs, in each case for the flow compensated recording sequence, or a speed encoding. The pixel matrix 70 can have columns 88-90, which comprise the pixel values of the MR image for the different speed encodings for one time period.

The pixel matrix 70 can have numerous groups 71-73 of columns. The number of groups 71-73 can be equal to the number $N_t$ of time periods, for which the data acquisition is executed.

Each of the groups 71-73 can have numerous columns, which are allocated to the reference MR image with flow compensation and to the at least one MR image with speed encoding. Each of the groups 71-73 can have ($N_v$+1) columns, wherein $N_v$ is the number of different speed encodings. As an example, $N_v$=3 can be a data acquisition with three different speed encodings in three directions that are orthogonal to one another, and for a recording with flow compensation for each time period. Values of $N_v$=1, $N_v$=2, or a value for $N_v$ that is greater than three can also be used.

The pixel matrix 70 has matrix elements that are pixel values of the first MR image 61. These matrix elements can be contained in a column 81 of the pixel matrix 70. The column 81 can contain all of the pixel values of the first MR image 61. The pixel matrix 70 has matrix elements that represent the pixel values of the second MR image 62 that is recorded in the first time period, but with a different speed encoding than that for the first MR image. These matrix elements can be contained in a further column 82 of the pixel matrix 70. The further column 82 can contain all of the pixel values of the second MR image 62. The pixel matrix 70 has matrix elements that represent the third MR image 63, which is recorded in another time period, but with the same speed encoding as the first MR image. These matrix elements can be contained in a further column 88 of the pixel matrix 70. The further column 88 can contain all of the pixel values of the third MR image 63.

The matrix elements of the pixel matrix 70 are determined with methods and apparatuses according to embodiment examples, in that first the matrix elements of at least two matrices are determined, the sum of which is the pixel matrix 70. For this, a first matrix L and a second matrix S can be determined such that the sum of the first matrix L and the second matrix S is the pixel matrix. The first matrix L and the second matrix S can be determined such that the first matrix L fulfills a first condition, which ensures that the first matrix L primarily represents signal portions that do not vary as a function of time and as a function of the speed encoding. The first matrix L and the second matrix S can be determined such that the second matrix S fulfills a second condition, which ensures that the second matrix S primarily represents signal portions from regions with flowing nuclear spins, which vary as a function of time and as a function of the speed encoding.

With methods and apparatuses according to embodiment examples, the first matrix L and the second matrix S are first determined, dependent on the raw data, by means of an iterative reconstruction. Subsequently, matrix elements of the pixel matrix M are determined therefrom.

FIG. 5 illustrates a first matrix 100, which is determined with methods and apparatuses according to embodiment examples. The first matrix 100 can be determined so as to be a matrix of a low order.

The first matrix 100 has numerous columns. The first matrix 100 can have numerous groups of columns 101-103. The number of groups 101-103 can be equal to the number $N_t$ of time periods for which the data acquisition is carried out. Each of the groups 101-103 can comprise numerous columns, which are allocated to the reference MR image with the flow compensated recording sequence and the at least one MR image with speed encoding. Each of the groups 101-103 can have ($N_v$+1) columns, wherein $N_v$ is the number of different speed encodings. As an example, $N_v$=3 can be for a data acquisition having three different speed encodings in three directions that are orthogonal to one another, and for a data acquisition with flow compensation for each time period.

The first matrix 100 has matrix elements in which the signal portions, which can vary as a function of time and as a function of the speed encoding, are suppressed. As an example, the first matrix 100 can have matrix elements that represent the pixel values for the stationary tissue 64 in the first MR image 61. The corresponding pixel values can be contained in a first column 104 of the first matrix 100. The first matrix 100 can have matrix elements that represent pixel values for the stationary tissue 64 in the second MR image 62. The corresponding pixel values can be contained in a second column 105 of the first matrix 100. The first matrix 100 can have matrix elements that represent the pixel values for the stationary tissue 64 in the third MR image 63.

The corresponding pixel values can be contained in a third column 106 of the first matrix 100.

The first matrix 100 can be determined such that the data regarding regions 65-67, which provide signal portions that can vary as a function of time and as a function of the speed encoding, are suppressed.

The data regarding the regions 65-67 do not need to be fully removed in the first matrix 100, but are contained with only small weights. The first matrix 100 can be determined such that the columns 101-103 of the first matrix 100 contain only a small amount, or none at all, of information regarding the regions 65-67 with flowing nuclear spins. This can be ensured by a first condition that the first matrix 100 must satisfy. As an example, in the determination of the first matrix 100, it can be ensured by means of a regularization term that an order for the first matrix 100 and/or a nuclear noun for the first matrix 100 fulfills a predefined criterion. As an example, the first matrix 100 can be determined under the first condition, that the order of the first matrix 100 is less than a threshold value and/or that the nuclear norm of the first matrix 100 is less than a threshold value.

Figure 6:
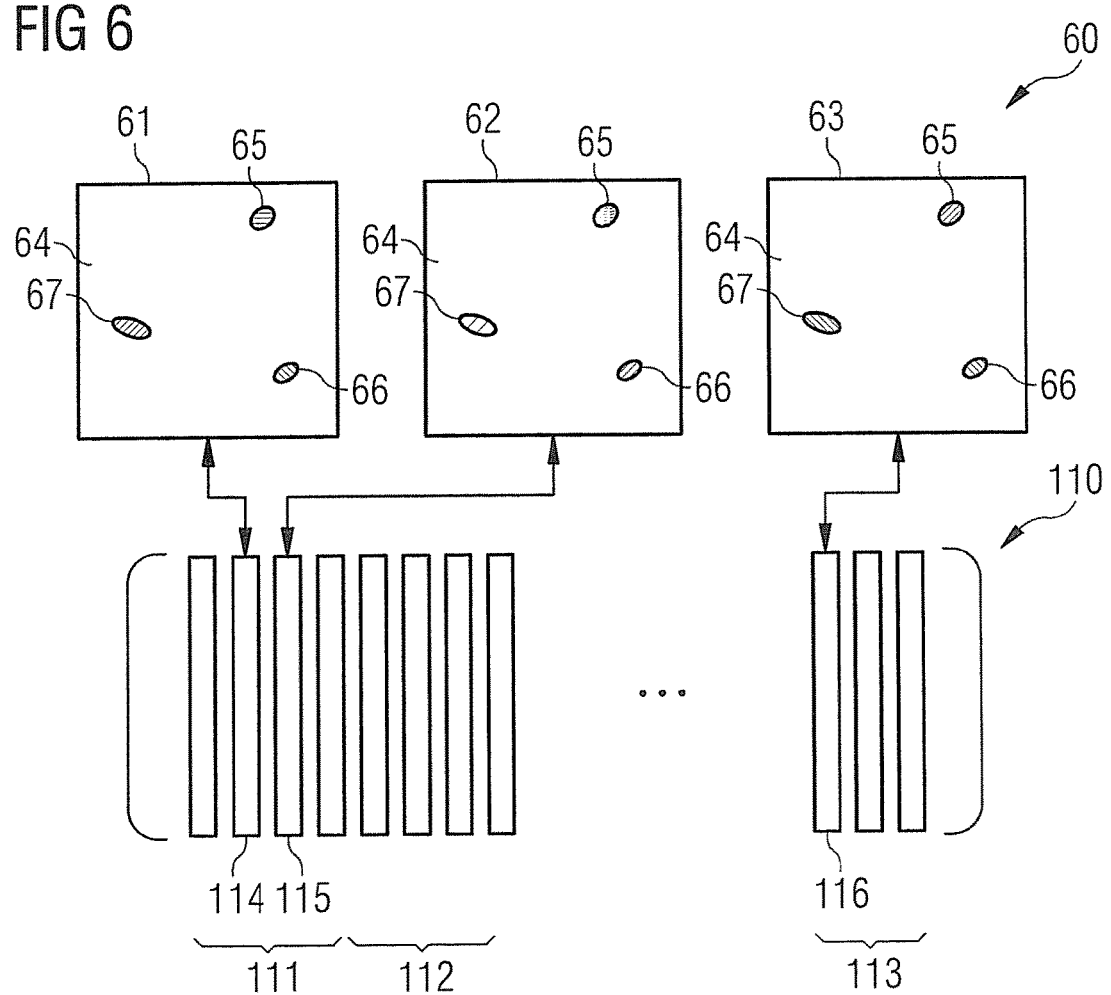
FIG. 6 illustrates a second matrix, which is determined, in an iterative reconstruction in an embodiment of the method according to the invention.

FIG. 6 illustrates a second matrix 110, which is determined with methods and apparatuses according to embodiments of the invention. The second matrix 110 can be determined such that the second matrix 110 can be transformed into a sparsely populated matrix. The second matrix 110 can be determined such that signal portions are suppressed therein, which do not vary as a function of time and as a function of the speed encoding.

The second matrix 110 has numerous columns. The second matrix 110 can have numerous groups 111-113 of columns. The number of groups 111-113 can be equal to the number $N_t$ of time periods for which data acquisition is carried out. Each of the groups 111-113 can comprise numerous columns, which are allocated to the reference MR image with the flow compensated recording sequence and the at least one MR image with speed encoding. Each of the groups 111-113 can have ($N_v$+1) columns, wherein $N_v$ is the number of different speed encodings. As an example, $N_v$=3 can be for a data acquisition with three different speed encodings in three directions that are orthogonal to one another, and for a data acquisition with flow compensation for each time period.

The second matrix 110 has matrix elements that represent signal contributions from regions 65-67, with flowing nuclear spins that vary as a function of time and as a function of the speed encoding. As an example, the second matrix 110 can have matrix elements that represent the pixel values for the regions 65-67 with flowing nuclear spins in the first MR image 61. The corresponding pixel values can be contained in a first column 114 of the second matrix 110. The second matrix 110 can have matrix elements that represent the pixel values for the regions 65-67 with flowing nuclear spins in the second MR image 62. The corresponding pixel values can be contained in a second column 115 of the second matrix 110. The second matrix 110 can have matrix elements that represent the pixel values for the regions 65-67 with flowing nuclear spins in the third MR image 63. The corresponding pixel values can be contained in a third column 116 of the second matrix 110.

The second matrix 110 can be determined such that it still contains data regarding the stationary tissue 64. The second matrix 110 can also be determined such that the data that does not vary as a function of time and as a function of the speed encoding, and is therefore redundant, which concerns the stationary tissue 64, can be removed by means of a suitable transformation. For example, in the determination of the second matrix 110, it can be ensured by means of a regularization term that the second matrix 110 is sparsely populated, or can be transformed into a sparsely populated matrix. Through the second regularization term, it is ensured that an $L_1$ norm for matrix elements of the second matrix 110 fulfills a predefined criterion after a wavelet transformation and/or a TV norm of a wavelet transformation of matrix elements of the second matrix 110 fulfills a predefined criterion. Other criteria can be used to ensure that the second matrix 110 can be transformed into a sparsely populated matrix.

The second matrix 110 does not necessarily have to be sparsely populated, but is determined such that it can be transformed into a sparsely populated matrix by means of a suitable transformation. The corresponding transformation, which is referred to in the technology as a so-called "sparsifying transformation," can, for example, comprise a wavelet transformation. The corresponding transformation can comprise the calculation of differences between columns in the second matrix 110, which are allocated to different time periods, but each correspond to the flow compensated recording sequence or each correspond to the same speed encoding.

Figure 7:
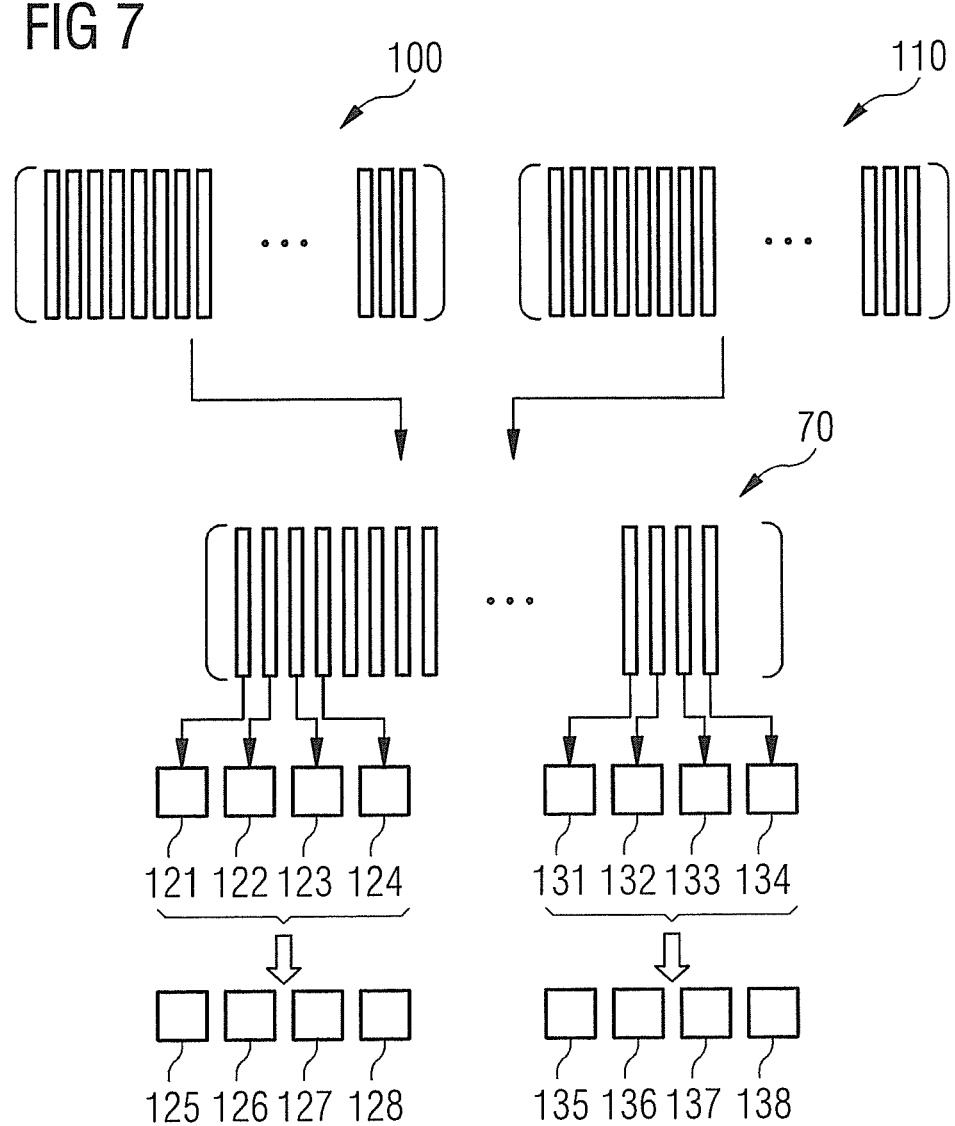
FIG. 7 illustrates the operating mode of a reconstruction in an embodiment of the method according to the invention.

FIG. 7 illustrates the mode of operation for methods and apparatuses according to embodiment examples in the reconstruction of MR images.

For this purpose, matrix elements of a first matrix 100 and matrix elements of a second matrix 110 are first determined. The determination of the matrix elements of the first matrix 100 and the matrix elements of the second matrix 110 occurs such that the matrix elements of the sum of the first matrix 100 and the second matrix 110 reproduce well the acquired raw data (not depicted in FIG. 7) after a transformation in the raw data space.

The matrix elements of the first matrix 100 and the matrix elements of the second matrix 110 can be determined such that the sum of the first matrix 100 and the second matrix 110 results in the pixel matrix. The pixel matrix has pixel values from MR images as matrix elements for numerous time periods and for different speed encodings, which reproduce well the acquired raw data after a transformation in the raw data space. The matrix elements of the first matrix 100 and the matrix elements of the second matrix 110 can be determined such that the first matrix 100 is a matrix having a low order, the matrix elements of which primarily represent signal portions that do not vary as a function of time and as a function of the speed encoding. The matrix elements of the first matrix 100 and the matrix elements of the second matrix 110 can be determined such that the second matrix can be transformed into a sparsely populated matrix, which contains data regarding the signal portions that can vary as a function of time and as a function of the speed encoding, from regions having flowing nuclear spins.

In order to determine a matrix element of a pixel matrix 70, one matrix element of the first matrix 100 and one matrix element of the second matrix 110 are added together in each case. All of the matrix elements of the pixel matrix 70 can be determined in this manner. The pixel matrix 70 can be determined as the sum of the first matrix 100 and the second matrix 110.

The pixel matrix 70 has N matrix elements for each of the time periods for which a data acquisition occurs, in each case for the flow compensated recording and for each speed encoding, which can be disposed, for example, in a column or a row of the pixel matrix. These matrix elements are the N pixel values of an MR image for the corresponding time period and the corresponding speed encoding.

Accordingly, the pixel values for all pixels of an MR image 121 for the flow compensated recording sequence, and the pixel values for all pixels of at least one MR image 122-124 with speed encoding, can be read out from the pixel matrix 70 for a first time period. A space-resolved speed data, dependent on the first matrix and the second matrix, can be determined. For this purpose, at least one phase contrast image 126-128, for example, can be calculated. The at least one phase contrast image can have pixel values that are, in each case, a difference of a phase of a pixel value of one of the MR images 122-124 with speed encoding, and a phase of a pixel value of the corresponding pixel in the reference MR image 121. Alternatively, or additionally, an anatomic image can be determined, in that, for example, for each pixel, the respective quantity, or the square of the quantity, of the difference of the pixel value of an MR image 122-124 with speed encoding and the pixel value for the reference MR image 121 is calculated. The squares of the quantities can be added together under the different speed encodings. The square root of the sum of the squares of the quantities of the differences between complex pixel values can provide the pixel value of the corresponding anatomic image 125. In this manner, a speed datum can be determined in a space-resolved manner.

In a similar manner, The pixel values for all pixels of an MR image 131 for the flow compensated recording, and the pixel values for all pixels of at least one MR image 132-134 with speed encoding can be read out from the pixel matrix 70 for at least one further time period. By means of the calculation of at least one phase contrast image 136-138 and/or one anatomic image 135, a speed datum can be determined in a space-resolved manner. The at least one phase contrast image 136-138 and/or the anatomic image 135 can be calculated from the at least one MR image 132-134 with speed encoding and the reference MR image 131.

The matrix elements of the first matrix 100 and the matrix elements of the second matrix 110 can be determined in an iterative procedure with methods and apparatuses according to embodiment examples. The matrix elements of the first matrix 100 and the matrix elements of the second matrix 110 can be determined in an iterative reconstruction, in which a deviation, between the acquired raw data and the raw data expected in the raw data space, after a transformation of the sum of the first matrix 100 and the second matrix 110, can be minimized under at least one co-condition for the first matrix 100 and/or the second matrix 110.

In a matrix form, the first matrix L can be as follows:

$$L = \begin{pmatrix} l_1^{1,0} & l_1^{1,1} & \cdots & l_1^{1,Nv} & l_1^{Nt,0} & l_1^{Nt,1} & \cdots & l_1^{Nt,Nv} \\ \vdots & \vdots & \ddots & \vdots & \cdots & \vdots & \vdots & \ddots & \cdots \\ l_N^{1,0} & l_N^{1,1} & \cdots & l_N^{1,Nv} & l_N^{Nt,0} & l_N^{Nt,1} & \cdots & l_N^{Nt,Nv} \end{pmatrix} \quad (3)$$

In this notation, the matrix element $l_i^{t,v}$ depicts an addend of the sum breakdown of a pixel value for the MR image in the time period t and with the speed encoding v. The index i indicates a position of the pixel in the MR image. The variable $N_t$ is a whole number, wherein $N_t$ is the number of time periods for which a data acquisition occurs. The index v can have the value 0 for a data acquisition with a flow compensated recording sequence, and the values $v=1, \ldots, N_v$, can represent a data acquisition with speed encoding, wherein $N_v$ is a whole number, indicating the number of recordings with different speed encodings.

In a matrix depiction, the second matrix S can be depicted as follows:

$$S = \begin{pmatrix} s_1^{1,0} & s_1^{1,1} & \cdots & s_1^{1,Nv} & s_1^{Nt,0} & s_1^{Nt,1} & \cdots & s_1^{Nt,Nv} \\ \vdots & \vdots & \ddots & \vdots & \cdots & \vdots & \vdots & \ddots & \cdots \\ s_N^{1,0} & s_N^{1,1} & \cdots & s_N^{1,Nv} & s_N^{Nt,0} & s_N^{Nt,1} & \cdots & s_N^{Nt,Nv} \end{pmatrix} \quad (4)$$

In this notation, the matrix element $s_i^{t,v}$ indicates another addend of the sum breakdown of a pixel value for the MR image in the time period t and with the speed encoding v. The index i indicates a position of the pixel in the MR image.

The first matrix L and the second matrix S can be determined by means of solving an optimization problem having the form:

$$D(L+S,A,y)+R_1(L)+R_2(S) \quad (5)$$

D(*) indicates a so-called data fidelity term thereby, which is a measure for how strong the deviation is between the acquired raw data, which can be compiled in a vector y, and the raw data expected for the sum of the first matrix L and the second matrix S. The expected raw data can be determined by imaging the sum of the first matrix L and the second matrix S in the raw data space using an imaging matrix A. If a data acquisition occurs in parallel with numerous receivers, this is taken into account by the imaging matrix A.

In equation (5), $R_1(L)$ indicates a first regularization term. The first regularization term $R_1(L)$ can be dependent on the matrix elements of the first matrix L. The first regularization term $R_1(L)$ can be independent of matrix elements of the second matrix S. The first regularization term $R_1(L)$ can be selected such that matrix elements of the first matrix L mainly represent signal portions that do not vary, or vary only slightly, as a function of time and over various speed compensated and speed encoded recordings. The first regularization term $R_1(L)$ can be selected such that the order of the matrix L is low, e.g. less than a threshold value. In addition, the first regularization term $R_1(L)$ can be selected such that a nuclear norm of the first matrix L is low, e.g. less than a threshold value.

In equation (5), $R_2(S)$ indicates a second regularization term. The second regularization term $R_2(S)$ can be dependent on matrix elements of the first matrix S. The second regularization term $R_2(S)$ can be independent of the first matrix L. The second regularization term $R_2(S)$ can be selected such that matrix elements of the second matrix S mainly represent data regarding signal portions that can vary as a function of time and over different speed compensated and speed encoded recordings, and that are present in smaller regions of each MR image. The second regularization term $R_2(S)$ can be selected such that the second matrix S can be transformed into a sparsely populated matrix.

The matrix elements of the first matrix L and the matrix elements of the second matrix S can be determined as a solution of the following problem:

$$\vec{l} = \begin{pmatrix} l_1^{1,0} \\ \vdots \\ l_N^{1,0} \\ l_1^{1,1} \\ \vdots \\ l_1^{Nt,Nv} \end{pmatrix} \quad (7)$$

The matrix elements of the first matrix L and the matrix elements of the second matrix S can be determined such that the function of equation (5) is minimized.

The matrix elements of the first matrix can be compiled in a vector having the dimension $N_t*(N_v+1)*N$. This vector can be depicted, for example, as:

$$\underset{L,S}{\arg\min}\{D(L+S, A, y) + R_1(L) + R_2(S)\} \quad (6)$$

Accordingly, the matrix elements of the second matrix S can be compiled in a vector having the dimension $N_t*(N_v+1)*N$. This vector can be depicted, for example, as:

$$\vec{s} = \begin{pmatrix} s_1^{1,0} \\ \vdots \\ s_N^{1,0} \\ s_1^{1,1} \\ \vdots \\ s_1^{Nt,3} \end{pmatrix} \quad (8)$$

The data fidelity term $D(*)$ in equation (5) and equation (6) can be defined, for example, as:

$$D(L+S,A,y) = \|A(\vec{s}+\vec{l}) - \vec{y}\|_{L_2}^2 \quad (9)$$

In the raw data vector, $\vec{y}$ are the raw data acquired in the raw data space with the at least one receiver 14a-14c for the numerous time periods, in each case for the flow compensated recording sequence and the at least one data acquisition with speed encoding, contained therein as vector elements.

The $L_2$ norm is indicated by $\|\cdot\|_{L_2}$.

The image matrix A images the elements of the sum of the first matrix L and the second matrix S, written as vector sum $(\vec{s}+\vec{l})$, in the raw data space. The image matrix A can be depicted in the following block form:

$$A = \begin{pmatrix} A^{1,0} & & & & & \\ & \ddots & & & & \\ & & A^{1,Nv} & & & \\ & & & \ddots & & \\ & & & & A^{Nt,0} & \\ & & & & & \ddots \\ & & & & & & A^{Nt,Nv} \end{pmatrix} \quad (10)$$

In equation (10), the entries outside the matrices $A^{t,v}$, that are disposed along the diagonals, are each equal to 0. The image matrix A is a block diagonal matrix. The matrix $A^{t,v}$ indicates the image of an image space in the raw data space for the time period t and for a recording sequence thereby, that can either be flow compensated (v=0) or can implement a speed encoding (v=1, ..., $N_v$).

The matrices $A^{t,v}$ can each be computationally dependent on a sub-scanning, which can be dependent on the time t and the speed encoding v, and are determined as a function of a matrix of Fourier coefficients. The matrices can furthermore be dependent on the sensitivity chart of the at least one receiver 14a-14c, in particular the sensitivity charts of numerous receivers in the case of parallel data acquisitions. The matrices $A^{t,v}$ are determined according to the following schematic formula:

$$A^{t,v} = U^{t,v}FC^t. \quad (11)$$

In equation (11), $C^t$ indicates the sensitivity charts for numerous receivers 14a-14c. The matrix F indicates the matrix of Fourier coefficients for the imaging of an image space in the raw data space. The matrix $U^{t,v}$ defines the respective sub-scanning pattern used as a function of the time period and the recording sequence, which can either be flow compensated (v=0) or can implement a speed encoding (v=1, ..., $N_v$). The sub-scanning pattern can be selected such that it can vary as a function of time and/or as a function of the index v, which indicates whether the recording sequence is flow compensated or implements a speed encoding. The sub-scanning patterns selected for different t's and/or different v's can be nested in one another.

The determination of the matrices $A^{t,v}$ according to equation (11) is known to the person skilled in the art, and shall not be described in detail here. In particular, the computational determination of the sensitivity charts $C^t$ and/or the determination of the sensitivity chart $C^t$ by means of measurements are known to those skilled in the art.

The matrix elements of the first matrix L and the matrix elements of the second matrix S can be determined by solving the optimization problem from equation (6). The matrix elements of the pixel matrix M can each be determined according to the following formula:

$$x_i^{t,v} = l_i^{t,v} + s_i^{t,v} \quad (12)$$

Phase contrast images can be calculated from the matrix elements of the pixel matrix M. As an example, a measure for the speed of flowing nuclear spins along a speed encoding direction, for which a data acquisition with a speed encoding v=1, ..., $N_v$ occurs, can be determined as the phase difference $$P_i^{t,v} = \arg(x_i^{t,0}) - \arg(x_i^{t,v}). \quad (13)$$

The function $\arg(*)$ in equation (13) indicates the phase for the complex pixel values $x_i^{t,0}$ and $x_i^{t,v}$.

An anatomic image with speed data at one location, which is imaged in a pixel i, can be determined as $$\tilde{P}_i^t = \sqrt{\Sigma_{v=1,\ldots,N_v} \|x_i^{t,0} - x_i^{t,v}\|^2}. \quad (14)$$

The first regularization term $R_1(L)$ in equations (5) and (6) can be established by different means, such that signal portions are suppressed in the first matrix L that can vary as a function of time and as a function of the speed encoding. The first regularization term can be selected such that it has a greater value for a first matrix having a larger number of linear independent column vectors than for a first matrix having a smaller number of linear independent column vectors.

As an example, the first regularization term $R_1(L)$ can be defined as follows:

$$R_1(L) = \alpha_3 \cdot \|L\|_*. \quad (15)$$

In equation (15), $\alpha_3 > 0$ indicates a positive real coefficient. The convex nuclear norm is indicated, in the conventional manner, with $\|\cdot\|_*$. The convex nuclear norm can be defined as the sum of the singular values in the first matrix L.

A complex singular value breakdown of the first matrix L can be defined as follows:

$$L = U\Sigma V^* \quad (16)$$

In equation (16), U is a unitary m×m matrix. V* is the conjugate of a unitary n×n matrix. The matrix Σ is an m×n diagonal matrix. The diagonal entries of the matrix Σ are positive and are the singular values of the first matrix L.

The convex nuclear norm of the first matrix L in equation (15) is:

$$\|L\|_* = tr(\Sigma) \tag{17}$$

The second regularization term $R_2(S)$ in equations (5) and (6) can be established by different means, such that signal portions are suppressed in the second matrix S that can vary little as a function of time and, optionally, also as a function of the speed encoding.

The second regularization term can be dependent on an $L_1$ norm of the second matrix S transformed with a transformation Φ. The transformation Φ can comprise a wavelet transformation. The transformation Φ can be a Fourier transformation and/or a time-dependent filtering. Alternatively, or additionally, the second regularization term $R_2(S)$ can be dependent on a TV norm for the second matrix S.

As an example, the second regularization term $R_2(S)$ can be defined as follows:

$$R_2(S) = \alpha_1 \cdot \|\vec{s}\|_{TV} + \alpha_2 \cdot \|\psi \vec{s}\|_{L_1} \tag{18}$$

In equation (18), $\alpha_1 \geq 0$ and $\alpha_2 \geq 0$ indicate real coefficients, at least one of which is greater than 0. The TV norm is indicated in the conventional manner with $\|\cdot\|_{TV}$. The $L_1$ norm is indicated in the conventional manner with $\|\cdot\|_{TV}$. The matrix representation of the transformation Φ is indicated with Ψ, with which the data are transformed into a sparsely populated matrix. As an example, Ψ can be the matrix representation of a wavelet transformation, with which the matrix elements of the second matrix S, which are compiled in the vector $\vec{s}$, can be transformed into matrix elements of a sparsely populated matrix.

The optimization problem defined by equations (5) and (6) can be solved in various ways. As an example, a split-Bregman method can be used. The optimization problem defined by equations (5) and (6) can be solved in an iterative procedure.

In the following, an exemplary implementation for an iterative solving procedure for the optimization problem defined by the equations (5), (6), (9), (15), and (18) shall be described. The matrix elements of the first matrix L and the matrix elements of the second matrix S shall be determined thereby by solving the following minimization problem:

$$\operatorname*{argmin}_{\vec{s},\vec{l}}\left\{\|A(\vec{s}+\vec{l})-\vec{y}\|^2_{L_2} + \alpha_1 \cdot \|\vec{s}\|_{TV} + \alpha_2 \cdot \|\psi \vec{s}\|_{L_1} + \alpha_3 \cdot \|L\|_*\right\} \tag{19}$$

For the iterative solution of the optimization problem from equation (19), the following auxiliary variables can be defined:

$$d_\nabla = \nabla(\vec{s}), \tag{20}$$

$$\vec{d}_w = \Psi(\vec{s}) \text{ and} \tag{21}$$

$$\vec{d}_n = \Xi(\vec{l}). \tag{22}$$

The Nabla operator is indicated thereby with $\nabla(\cdot)$. The transformation Ψ can be the matrix representation of a wavelet transformation, with which the matrix elements of the second matrix S, which are compiled in the vector $\vec{s}$, can be transformed into matrix elements of a sparsely populated matrix. The transformation Ξ indicates a transformation with which the matrix elements of the first matrix L compiled in the vector $\vec{l}$ are transformed into a domain having a low order.

Furthermore, the residual variables $\mu_\nabla$, $\mu_w$, and $\mu_n$ can be defined for the iterative solving procedure.

In the following, the iteration step for an iterative solving of the optimization problem of equation (19) shall be indicated with superscript indices.

The iterative solving procedure is initialized as follows:

$$\vec{l}^0 = \vec{s}^0 = 0, \tag{23}$$

$$d_\nabla^0 = 0, \tag{24}$$

$$\vec{d}_w^0 = 0, \tag{25}$$

$$\vec{d}_n^0 = 0, \tag{26}$$

$$\mu_\nabla^0 = 0, \tag{27}$$

$$\mu_w^0 = 0 \text{ and} \tag{28}$$

$$\mu_n^0 = 0, \tag{29}$$

In each iteration, new values for the different variables are determined as follows:

$$(\vec{s}^{k+1}, \vec{l}^{k+1}) = \operatorname*{argmin}_{\vec{s}^k, \vec{l}^k}\left\{\|A(\vec{s}^k+\vec{l}^k)-\vec{y}\|^2_{L_2} + \alpha_3 \cdot \|\vec{d}_n^k - \Phi(\vec{l}^k) - \mu_n^k\|^2_{L_2} + \alpha_1 \cdot \|\vec{d}_\nabla^k - \nabla(\vec{s}^k) - \mu_\nabla^k\|^2_{L_2} + \alpha_2 \cdot \|\vec{d}_w^k - \psi(\vec{s}^k) - \mu_w^k\|^2_{L_2}\right\} \tag{30}$$

$$(\vec{d}_\nabla^{k+1}) = \operatorname*{argmin}_{\vec{d}_\nabla^k}\left\{\|\vec{d}_\nabla^k - \nabla(\vec{s}^{k+1}) - \mu_\nabla^k\|^2_{L_2} + \|\vec{d}_\nabla^k\|_{TV}\right\} \tag{31}$$

$$(\vec{d}_w^{k+1}) = \operatorname*{argmin}_{\vec{d}_w^k}\left\{\|\vec{d}_w^k - \Psi(\vec{s}^{k+1}) - \mu_w^k\|^2_{L_2} + \|\Psi(d_w^k)\|_{L_1}\right\} \tag{32}$$

$$(\vec{d}_n^{k+1}) = \operatorname*{argmin}_{\vec{d}_n^k}\left\{\|\vec{d}_n^k - \Xi(\vec{l}^{k+1}) - \mu_n^k\|^2_{L_2} + \|\Xi(d_n^k)\|_*\right\} \tag{33}$$

The Nabla operator for the TV norm is indicated by $\nabla(\cdot)$. In equation (31), $\|\cdot\|_{TV}$ indicates the TV norm.

With the iterative solution, the up-dated matrix elements for the first matrix L and the second matrix S are first determined in each iteration according to equation (30), in a first sub-step. For this, the up-dated vectors $\vec{s}^{k+1}$ and $\vec{l}^{k+1}$ are determined such that the right-hand side of the equation (30) is minimized.

The updated vectors $\vec{s}^{k+1}$ and $\vec{l}^{k+1}$ determined in this manner are subsequently used in equations (31)-(33), in order to up-date the auxiliary variables $d_\nabla$, $\vec{d}_w$, and $\vec{d}_n$. Depending on the different regularization terms, different respective, adjusted actualization steps can be used thereby, as depicted in equations (31)-(33).

With the minimization of the terms dependent on the nuclear norm, a threshold value comparison of the singular values can occur (a so-called "Singular Value Thresholding" procedure). As an example, the complex singular value breakdown for the up-dated first matrix $L^{k+1}$, which contains the vector elements for the vector $\vec{l}^{k+1}$ in a matrix depiction according to equations (3) and (7), can be determined according to the following equation:

$$L^{k+1} = U\Sigma V^* \quad (34)$$

The diagonal elements $\sigma_{i,i}$ of the diagonal matrix $\Sigma$ can be subjected to a threshold value comparison. A modified diagonal matrix $$\vec{\Sigma} = \text{diag}(\vec{\sigma}_{i,i}) \quad (35)$$

can be determined, wherein $$\bar{\sigma}_{i,i} = \sigma_{i,i} \text{ if } \sigma_{i,i} \geq \epsilon \text{ and} \quad (36)$$

$$\bar{\sigma}_{i,i} = 0 \text{ if } \sigma_{i,i} < \epsilon. \quad (37)$$

In equations (37) and (38), $\epsilon$ indicates a threshold value, which can be constant.

The new matrix elements of the first matrix L and be re-calculated as $$L^{k+1} = U\bar{\Sigma}V^*. \quad (38)$$

Subsequently, in a last sub-step, each iteration of the residual variables can be up-dated as follows:

$$\mu_\nabla^{k+1} = \mu_\nabla^k + \nabla(\vec{s}^{k+1}) - \vec{d}_\nabla^{k+1}, \quad (39)$$

$$\mu_\psi^{k+1} = \mu_\psi^k + \Psi(\vec{s}^{k+1}) - \vec{d}_\psi^{k+1} \text{ and} \quad (40)$$

$$\mu_n^{k+1} = \mu_n^k + \Xi(\vec{l}^{k+1}) - \vec{d}_n^{k+1}. \quad (41)$$

Subsequently, the next iteration step can be executed.

Figure 8:
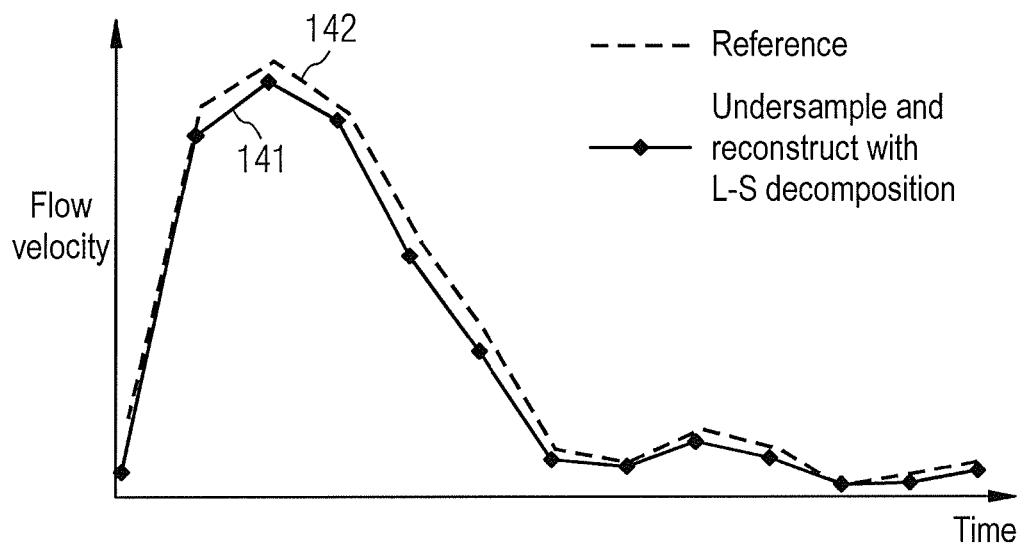
FIG. 8 shows time-resolved flow measurement values determined in an embodiment of the method according to the invention.

FIG. 8 shows results that are obtained with methods and MR apparatuses according to embodiment examples, with a sub-scanning of the raw data space, in comparison with results obtained with a complete scanning of the raw data space as a reference. The data obtained from the complete scanning of the raw data space are depicted as the reference curve 142.

The flow speed 141 is determined with methods and MR apparatuses according to embodiment examples. A sub-scanning of the raw data space during the data acquisition is carried out in combination with the determination of a sum breakdown of the pixel matrix during the iterative reconstruction. The determined time-dependent flow speeds 141 reproduce the reference curve 142 well. The time required on the whole for the data acquisition can be substantially reduced for methods and MR apparatuses according to embodiment examples, in comparison with a complete scanning of the raw data space.

While methods and apparatuses are described according to embodiment examples, modifications can be implemented in further embodiment examples. As an example, a smaller or larger number of sequences with different speed encodings can also be used in each time period. It is possible to record only two raw data sets, corresponding to one recording with flow compensation, and one recording with speed encoding. Six or more raw data sets can also be recorded, corresponding to one flow compensated sequence, and at least five flow sensitive sequences. Numerous raw data sets with flow compensation can also be recorded for each time period. As an example, for each speed encoding, raw data can also be acquired for a recording with flow compensation in each case.

While the iterative reconstruction can be executed such that with each iteration, both up-dated values for the matrix elements of the first matrix as well as up-dated values for the matrix elements of the second matrix are calculated, in further embodiment examples the up-dated values for the matrix elements of the first matrix and/or the up-dated values for the matrix elements of the second matrix can be determined in each $k^{th}$ iteration, wherein k is a whole number, and k>1.

While the iterative reconstruction can be executed using a split-Bregman technique, other iterative techniques can also be used, with which matrix elements of a first matrix and a second matrix are determined as a solution of an optimization problem, subject to co-conditions.

While certain designs for matrices and vectors, which contain matrix elements, have been described in order to explain the iterative reconstruction, numerous other designs can be used in further embodiment examples. As an example, the different pixel values of an MR image can each be contained in a respective row of a matrix.

While methods and apparatuses have been described, in which a breakdown of the pixel matrix is determined as a sum of a first matrix and a second matrix, the techniques can also be used in order to determine a breakdown of the pixel matrix into more than two addends.

Methods and MR apparatuses according to embodiment examples can be used, in particular, for phase contrast angiography.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for phase contrast magnetic resonance (MR) imaging with speed encoding, comprising:
   operating an MR data acquisition unit according to an MR data acquisition sequence wherein nuclear spins in an examination subject are excited, and MR signals are acquired therefrom in at least one time period, with raw data representing said MR signals being acquired in each time period for a plurality of MR images, with said plurality of MR images comprising a reference MR image with flow compensation and at least one MR image with speed encoding;
   providing said raw data to an image reconstruction computer and, in said image reconstruction computer, determining a plurality of matrices for each time period of said at least one time period such that the sum of said plurality of matrices is characterized by a pixel matrix with a plurality of matrix elements comprising matrix elements that represent pixel values for said reference MR image and other matrix elements representing pixel values for said at least one MR image with speed encoding, and such that a first matrix among said plurality of matrices fulfilling a predetermined first condition;
   using said plurality of matrices to reconstruct an image of the examination subject; and
   making said image of the examination subject available in electronic form at an output of said image reconstruction computer.

2. A method as claimed in claim 1 wherein said first condition is that signal contributions are suppressed in said first matrix that vary as at least one of a function of time or a function of said speed encoding.

3. A method as claimed in claim 1 wherein said first condition is dependent on an order of said first matrix.

4. A method as claimed in claim 3 wherein said first condition is that said order of said first matrix is less than a threshold value.

5. A method as claimed in claim 1 comprising determining the matrix elements of the respective matrices in said plurality of matrices by:
    determining matrix elements of said first matrix;
    determining matrix elements of a second matrix of said plurality of matrices; and
    forming said pixel matrix as a sum of said first matrix and said second matrix.

6. A method as claimed in claim 5 comprising determining said matrix elements of said second matrix such that said second matrix fulfills a predetermined second condition that differs from said predetermined first condition.

7. A method as claimed in claim 6 wherein said second condition is that said second matrix contains matrix elements representing raw data originating from flowing nuclear spins in said subject.

8. A method as claimed in claim 6 wherein said second condition is a requirement that said second matrix be transformable into a matrix populated with matrix elements having a population density that is below a threshold value.

9. A method as claimed in claim 5 comprising determining the matrix elements of said first matrix and the matrix elements of said second matrix by minimizing a target function, said target function comprising at least one first regularization term that is dependent on the matrix elements of the first matrix and at least one second regularization term that is dependent on matrix elements of said second matrix.

10. A method as claimed in claim 9 wherein said first regularization term is independent of the matrix elements of the second matrix, and wherein said at least one second regularization term is independent of the matrix elements of the first matrix.

11. A method as claimed in claim 9 wherein said first regularization term is dependent on a nuclear norm for said first matrix.

12. A method as claimed in claim 9 wherein said at least one second regularization term comprises at least one of total variation and a focalized variation of matrix elements of said second matrix.

13. A method as claimed in claim 9 wherein the matrix elements of the first matrix and the matrix elements of the second matrix are determined collectively in an iterative procedure.

14. A method as claimed in claim 1 comprising, from said pixel matrix, automatically determining speed data for said flowing nuclear spins in said time periods.

15. A method as claimed in claim 1 comprising detecting said MR signals for acquiring said raw data by entering the raw data into a memory organized as k-space, with said raw data not completely filling k-space.

16. A magnetic resonance (MR) apparatus for phase contrast magnetic resonance imaging with speed encoding, comprising:
    an MR data acquisition unit;
    a control computer configured to operate an MR data acquisition unit according to an MR data acquisition sequence wherein nuclear spins in an examination subject are excited, and MR signals are acquired therefrom in at least one time period, with raw data representing said MR signals being acquired in each time period for a plurality of MR images, with said plurality of MR images comprising a reference MR image with flow compensation and at least one MR image with speed encoding;
    an image reconstruction computer provided with said raw data, said image reconstruction computer being configured to determine a plurality of matrices for each time period of said at least one time period such that the sum of said plurality of matrices is characterized by a pixel matrix with a plurality of matrix elements comprising matrix elements that represent pixel values for said reference MR image and other matrix elements representing pixel values for said at least one MR image with speed encoding, and such that a first matrix among said plurality of matrices fulfilling a predetermined first condition;
    said image reconstruction computer being configured to reconstruct an image of the examination subject using said plurality of matrices; and
    said image reconstruction computer being configured to make said an image of the examination subject available in electronic form at an output of said image reconstruction computer.

* * * * *